(12) United States Patent
Shah et al.

(10) Patent No.: US 11,351,343 B2
(45) Date of Patent: Jun. 7, 2022

(54) INTRAVENOUS ACCESS ASSIST DEVICE WITH SAFETY FEATURE

(71) Applicants: Amit Shah, North Potomac, MD (US); Curt Kothera, Rockville, MD (US); Pablo Sztein, Silver Spring, MD (US)

(72) Inventors: Amit Shah, North Potomac, MD (US); Curt Kothera, Rockville, MD (US); Pablo Sztein, Silver Spring, MD (US)

(73) Assignee: INNOVITAL, LLC, Calverton, MD (US)

( * ) Notice: Subject to any disclaimer, the term of this patent is extended or adjusted under 35 U.S.C. 154(b) by 628 days.

(21) Appl. No.: 16/040,104

(22) Filed: Jul. 19, 2018

(65) Prior Publication Data

US 2018/0344985 A1    Dec. 6, 2018

Related U.S. Application Data

(63) Continuation-in-part of application No. 15/612,707, filed on Jun. 2, 2017, now abandoned.

(51) Int. Cl.
*A61M 25/06* (2006.01)
*A61M 5/32* (2006.01)

(52) U.S. Cl.
CPC .... *A61M 25/0606* (2013.01); *A61M 25/0631* (2013.01); *A61M 5/3245* (2013.01); *A61M 5/3273* (2013.01); *A61M 25/0625* (2013.01); *A61M 25/0693* (2013.01)

(58) Field of Classification Search
CPC .......... A61M 25/0606; A61M 25/0612; A61M 25/0625; A61M 25/0631; A61M 25/0618; A61M 25/06; A61M 25/01; A61M 2025/0681; A61M 2025/0687
See application file for complete search history.

(56) References Cited

U.S. PATENT DOCUMENTS

| | | | |
|---|---|---|---|
| 3,536,073 A | 10/1970 | Farb | |
| 4,108,175 A * | 8/1978 | Orton | A61M 25/0693 600/581 |
| 4,747,831 A | 5/1988 | Kulli | |
| 4,781,692 A | 11/1988 | Jagger et al. | |
| 4,832,696 A | 5/1989 | Luther et al. | |
| 5,137,517 A | 8/1992 | Loney et al. | |

(Continued)

FOREIGN PATENT DOCUMENTS

WO    WO-2007003874 A1 *  1/2007  ........ A61M 25/0625

*Primary Examiner* — Kevin C Sirmons
*Assistant Examiner* — Leah J Swanson
(74) *Attorney, Agent, or Firm* — Royal W. Craig; Gordon Feinblatt LLC

(57) ABSTRACT

The present invention is a simple-to-use IV placement assist device with an added safety feature. A catheter advancer is slidably integrated with a base to guide advancement of a catheter linearly along the insertion path of the needle and catheter. A safety feature is engaged by a movable component moving from a first position to a second position, such movable enabling relative movement between the base and catheter advancer and/or catheter assembly, rotation of the needle about its length axis, and/or minor advancement of the catheter assembly to sheath the tip of the needle. The IV placement assist device stabilizes and guides the critical needle insertion and catheter advancement steps of a complication-prone and very common procedure.

31 Claims, 10 Drawing Sheets

(56) References Cited

U.S. PATENT DOCUMENTS

| | | | | |
|---|---|---|---|---|
| 5,279,590 A * | 1/1994 | Sinko | ............... | A61M 25/0631 |
| | | | | 604/110 |
| 5,672,160 A * | 9/1997 | Osterlind | ........... | A61M 25/0631 |
| | | | | 604/263 |
| 5,700,250 A | 12/1997 | Erskine | | |
| 6,126,633 A | 10/2000 | Kaji et al. | | |
| 6,273,871 B1 | 8/2001 | Davis et al. | | |
| 6,620,136 B1 | 9/2003 | Pressly, Sr. et al. | | |
| 9,744,344 B1 | 8/2017 | Devgon et al. | | |
| 2003/0199827 A1* | 10/2003 | Thorne | ............. | A61M 25/0631 |
| | | | | 604/164.08 |
| 2014/0094774 A1* | 4/2014 | Blanchard | ......... | A61M 25/0097 |
| | | | | 604/506 |
| 2014/0276435 A1* | 9/2014 | Shaw | ............... | A61M 25/0693 |
| | | | | 604/164.12 |
| 2015/0305769 A1* | 10/2015 | Ibragimov | ........ | A61M 25/0606 |
| | | | | 606/180 |
| 2017/0043132 A1* | 2/2017 | Ishida | ............... | A61M 25/0606 |
| 2017/0120014 A1* | 5/2017 | Harding | ............... | A61M 39/04 |

\* cited by examiner

INTRAVENOUS ACCESS ASSIST DEVICE WITH SAFETY FEATURE

CROSS-REFERENCE TO RELATED APPLICATIONS

The present application is a continuation-in-part of U.S. patent application Ser. No. 15/612,707, filed 2 Jun. 2017, entitled "Intravenous Access Assist Device," which is hereby incorporated by reference herein in its entirety.

STATEMENT REGARDING FEDERALLY SPONSORED RESEARCH

This invention was made with U.S. Government support under Contract No. W81XWH-18-C-0068, awarded by USAMRAA. The U.S. Government has certain rights in this invention.

BACKGROUND OF THE INVENTION

Field of the Invention

The present invention relates to medical devices and, more particularly, a device for assisting a user in gaining vascular access of a patient.

Description of the Background

Venous access is among the critical first steps in caring for patients in the pre-hospital, emergency department/trauma center, and in-hospital environments. Fluid therapy and medication delivery rely on adequate intravenous (IV) access and, accordingly, 60-90% of hospitalized patients require a peripheral IV during their hospital stay. Over 300 million peripheral IV's are sold yearly in the US and over 1 billion units are sold worldwide. However, in 12-26% of adult patients and 24-54% of pediatric patients, the first attempt at catheter insertion fails, requiring additional, painful attempts. Moreover, blood vessel trauma resulting from failed insertion attempts increases the risk of subsequent catheter failure, with failure defined as catheter removal before the end of its intended dwell time or before the CDC recommended 72-96 hour dwell time limit. Peripheral IV's fail at a rate of 35-50% due to painful processes such as inflammation (phlebitis); fluid or medication leakage into surrounding tissue (infiltration); dislodgment mechanical failure (e.g., occlusion); and site or bloodstream infection. Unsuccessful IV insertion attempts and IV failures are expensive in terms of direct equipment costs; provider time; necessitating more invasive venous access procedures; management of complications; additional hospital days; and, of course, the patient's pain and dissatisfaction.

Providers with high levels of training and experience have a significantly higher first pass success rate and lower incidence of ultimate IV failure, both of which directly reduce the pain experienced by the patient. Of course, training and experience are, by their very nature, time-intensive and otherwise expensive to acquire. An innovative device that enables novices to mimic the fluid expert approach could be of great value, provided that it is rigorously designed to meet patient, disease process, user, environmental, size, weight, and cost requirements.

The past several years has seen innovation relevant to IV placement. Examples include ultrasound and near-infrared technologies to aid vessel identification; antibiotic-impregnated and other cleansing approaches to tubing, connectors and dressings; and novel approaches to catheter stabilization. However, little has been done to simplify the often difficult task of actual IV insertion. In fact, novel technologies often assume a baseline level of competency with IV placement—an assumption that is not supported by the literature cited above, nor recent reports of >20% nursing turnover and high nursing vacancy rates in emergency settings. Emergency Medical Services (EMS) providers also turn over frequently. Functionally, high turnover rates in emergency settings equate to less experienced providers attempting IV placement on patients who are often the most difficult to access (e.g., due to dehydration) and in the most immediate need. Again, a device that simplifies the most difficult aspects of IV insertion could be of value.

Several of the steps followed for IV insertion require precision and a steady hand to prevent the needle from going all the way through the vein. Senior nurses, and the literature, counsel new nurses to pay special attention to these steps, especially in patients who have difficult-to-access veins due to dehydration, excess or thin skin, scarring, obesity, and edema, among other conditions. As described in primers on IV placement written by nurse educators, the most common errors after appropriate target vessel identification and tourniquet placement are related to vein stabilization, angle of approach, and IV assembly advancement after a flash of blood is visualized, offering an opportunity for innovation.

Regarding related art, U.S. Pat. No. 4,832,696 to Luther et al. issued May 23, 1989 shows an assembly designed to permit the insertion of an "over-the-needle" catheter. U.S. Pat. No. 9,744,344 to Devgon et al. issued Aug. 29, 2017 shows a catheter introducer which, as shown in FIGS. 12-14, includes a set of ribs 436 distributed along at least a portion of the introducer 410 which vibrate the device to provide the user with a haptic, tactile, and/or audible indicator associated with a position of the catheter 460 relative to the introducer 410. U.S. Pat. No. 4,108,175 to Orton issued 22 Aug. 1978 shows a catheter insertion device that can be controlled entirely by one hand and which has a flash chamber. U.S. Pat. No. 6,620,136 to Pressly, Sr. et al. issued Sep. 16, 2003 shows a retractable I-V catheter placement device with a magnified transparent verification cavity in the needle hub for viewing blood flash. U.S. Pat. No. 3,536,073 to Farb discloses an enlarged needle having a bore of sufficient diameter to accommodate a catheter. The needle is secured to a plunger which is slidably mounted within housing. A tubular protective sheath is disposed intermediate the needle and the housing and the protective tubing can be advanced to surround the needle after it is withdrawn from the patient's body. U.S. Pat. No. 4,781,692 to Jagger, et al. discloses a protective arrangement for a catheter insertion needle wherein the needle is pulled into a protective position within a surrounding tube by a pulling force applied through a flexible tube. U.S. Pat. No. 5,279,590 to George E. Sinko et al. issued 19 Jan. 1994 shows a tubular catheter placement guide. After the catheter is advanced, the needle can be retracted into a housing and locked into place with a tab 20. United States Patent Application 20170120014 by Harding et al. published May 4, 2017 shows an intravenous catheter securement platform with a textured paddle grip. U.S. Pat. No. 5,700,250 to Erskine issued Dec. 23, 1997 shows a catheter-advancement system with a hollow barrel that houses a needle hub. A movable latch initially maintains the needle hub adjacent to the distal end of the barrel and then enables retraction of the needle into the barrel. U.S. Pat. No. 5,137,517 Loney et al. issued Aug. 11, 1992 shows an advancer for catheters or guidewires with a body having a longitudinal slot that fits a slidable insert. Moving the insert longitudinally relative to the body activates a slide arrangement. U.S. Pat. No. 6,273,871 to Davis et al. issued Aug. 14, 2001 shows a splittable catheter introducer having a pair of wings and an introducer needle. U.S. Pat. No. 6,126,633 to Kaji et al. issued Oct. 3, 2000 shows a needle applicator with markers 5 as indexes for the depth of insertion, which are arranged at regular intervals in the axial direction. Preferably, each interval ranges from 3 to 5 mm. U.S. Pat. No. 4,747,831 to Kulli discloses a needle operating assemblage which can be utilized for insertion of a cannula or over-the-needle catheter wherein the positioning of the needle in its operative opposition compresses a spring between a shoulder provided on the outer end of the needle and a latch mounted for radial movement relative to the housing. After the venipuncture is accomplished, depressing the latch permits the needle to be retracted by the spring to a position where in the pointed end of the needle lies within the end of the housing. Pending United States application 20150305769 by Ibragimov filed Apr. 28, 2014 shows an introducer catheter wherein the needle hub includes an actuator configured to rotate the needle by about half of a turn.

SUMMARY OF THE INVENTION

It is, therefore, an object of the present invention to provide an easy-to-use IV placement assist device that is designed to enhance safety and usability.

It is another object to provide an IV placement assist device that facilitates small movements of the needle/catheter assembly or either part individually, such as with advancement of the catheter over the needle, all without interrupting the flow of the IV start procedure or reducing tactile feedback.

It is another object of the invention to prevent unintended motion of the cannula or catheter relative to the needle.

It is an overarching object to provide an IV placement assist device with the foregoing qualities that facilitates a higher first attempt IV placement success rate and decreased vessel trauma and, as a result, decreased IV failures, increased patient comfort and satisfaction, and decreased cost.

In accordance with the foregoing objects, the invention disclosed herein is a simple-to-use IV placement assist device with a base, which is configured to be held by the user, a needle mounted in the base and extending distally therefrom with a sharp incising end, a catheter advancer slidably integrated with the base, a catheter assembly comprising a distal catheter and proximal hub, which slides over the needle and interfaces with the distal end of the catheter advancer, and another movable component that engages and initiates one or more operational safety features, which may be designed into the aforementioned parts or enabled by other parts. These operational safety features may include but are not limited to any one or combination of a lock that prevents motion of the catheter advancer, a lock that prevents motion of the catheter assembly, a mechanism that translates the catheter such as to sheath the needle tip, and a rotation of the needle about its length axis. The needle is generally fixed relative to the base and specifically does not retract. The catheter advancer is movable distally about the generally fixed needle as it pushes the catheter assembly distally, and is configured to encompass the needle in the fully advanced position, acting as a needle guard, another operational safety feature of the device (albeit not engaged by the movable component).

The foregoing components combine to form an integrated assistive device of the present invention. The result is an easy-to-use, handheld device that can stabilize and guide the critical needle insertion and catheter advancement steps of a complication-prone and very common procedure. The base serves as a stabilizing component that emanates from the user's hand, designed to function as an extension of his/her fingers. This component, which is the needle hub of the device, provides the user with means of gripping and controlling the typically small needle hub, as well as providing clear view of the flash chamber at the proximal end of the needle. The catheter advancer component slidably integrates with the base component and may lock into place surrounding the needle after completion of the catheter advancement step of the IV insertion procedure. Engagement between the catheter advancer and the catheter assembly is generally not tight, so the component can be freely removed from the inserted catheter without any possibility of dislodging the catheter. There may be means that prevent the catheter assembly from rotating relative to the catheter advancer during the advancement process.

BRIEF DESCRIPTION OF THE DRAWINGS

Other objects, features, and advantages of the present invention will become more apparent from the following detailed description of the preferred embodiment and certain modifications thereof when taken together with the accompanying drawings in which.

DETAILED DESCRIPTION OF THE PREFERRED EMBODIMENT

The present invention is an IV placement assist device for assisting in the manual placement of an IV catheter without interrupting the flow of the IV start procedure.

Figure 1:
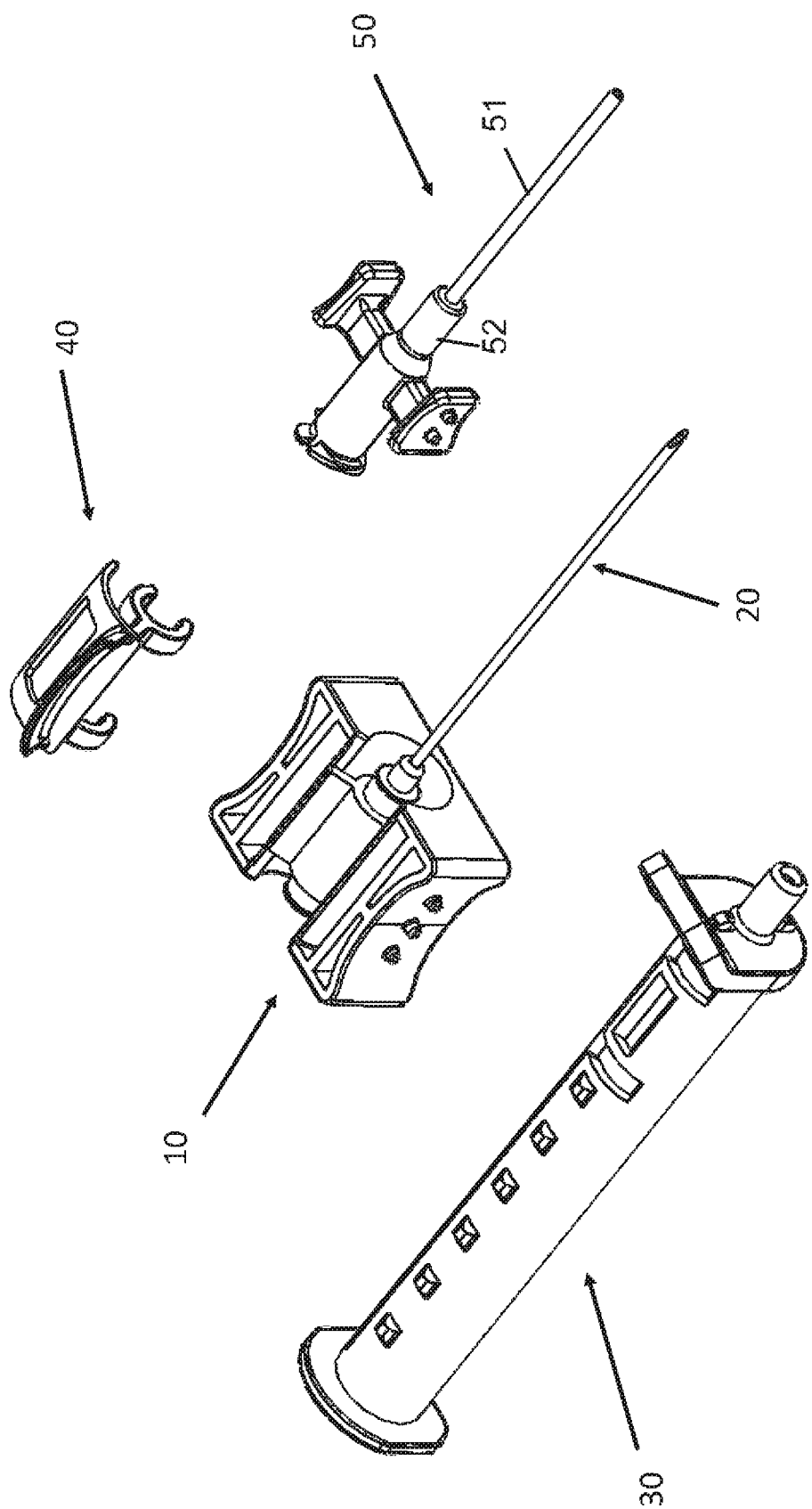
FIG. 1 is a top perspective illustration of an exploded view of the intravenous access assist device of the present invention.
Figure 2:
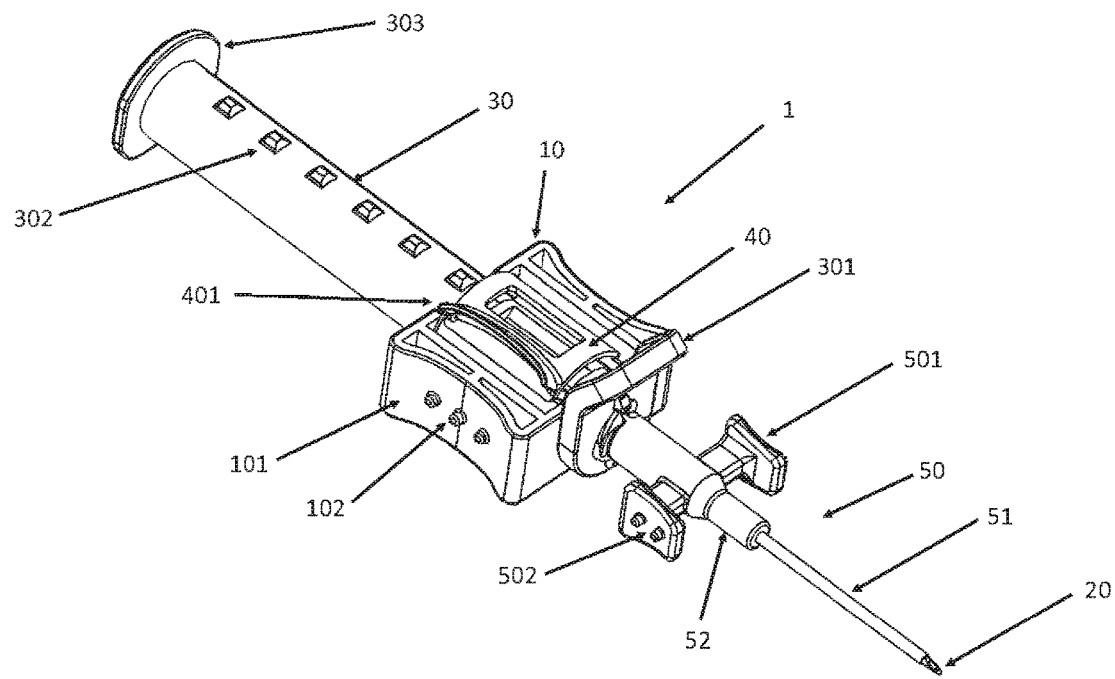
FIG. 2 is a top perspective illustration of the intravenous access assist device of the present invention in the "starting" configuration.
Figure 3:
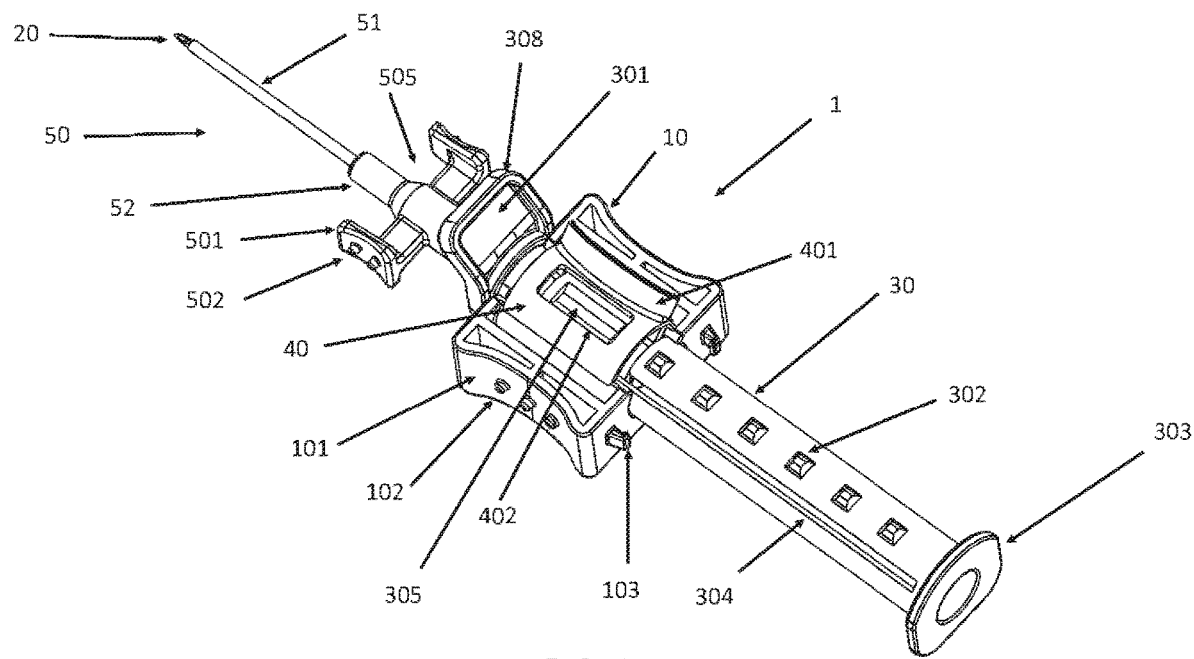
FIG. 3 is an alternative top perspective illustration of the intravenous access assist device of the present invention in the "starting" configuration.
Figure 4:
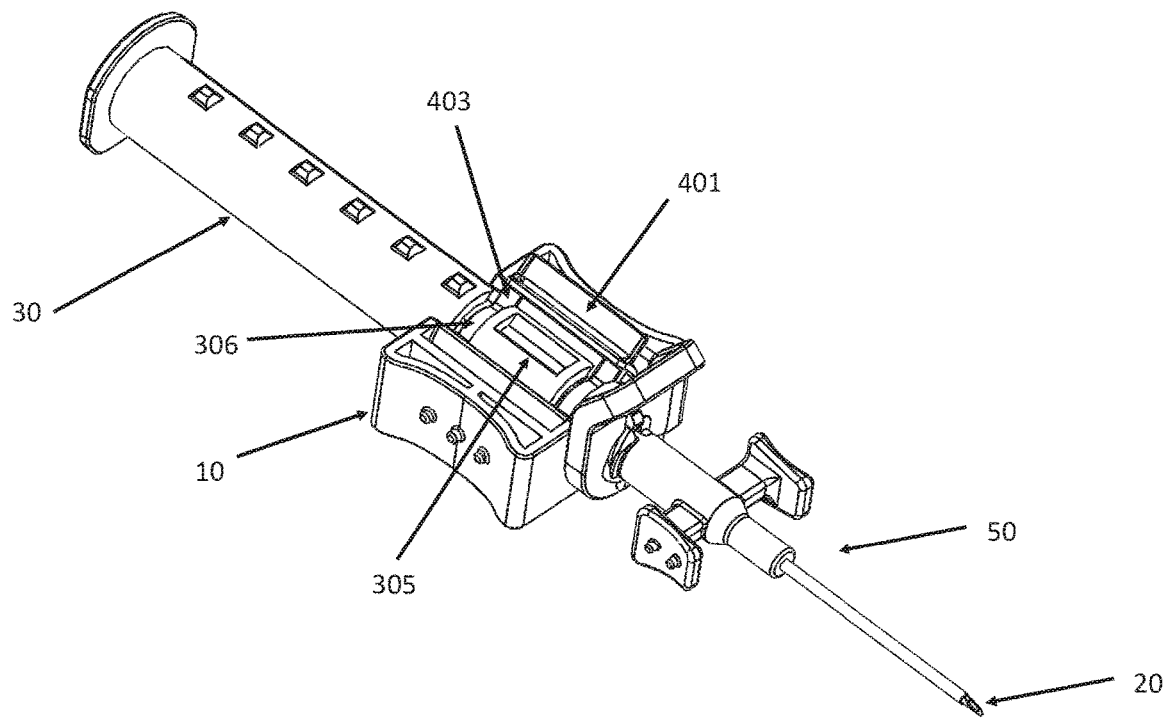
FIG. 4 is a top perspective illustration of the intravenous access assist device of the present invention in the "ready to advance" configuration.

With reference to FIG. 1, the IV placement assist device 1 generally comprises a base 10, a needle 20, a catheter advancer 30, a movable component 40, and a catheter assembly 50. The catheter assembly 50 is comprised of a distal catheter 51 and a proximal hub 52 (see also FIG. 2).

In reference to FIGS. 2-6, base 10 preferably has sidewardly-gripped and contoured finger interfaces 101 oriented on the lateral faces of base 10 such that the user can hold base 10 with a squeeze grip between the thumb and middle finger. Finger interfaces 101 also preferably provide a wide grip such that the tips of the thumb and middle finger are spaced wide enough apart to clearly see between them, even for a gloved user with large fingers. To facilitate gripping, finger interfaces 101 are preferably concave and may contain additional features such as protrusions 102 for tactile feedback and control. Other patterned protrusions, indentions, and textures may also be used within the same invention.

Base 10 is intended to mechanically engage the catheter advancer 30 and such mechanical engagement allows the generally cylindrical body of catheter advancer 30 to slide within a conforming channel 104 of base 10. The cross-sectional shape of catheter advancer 30 is preferably cylindrical, though this is not intended to be limiting to the invention inasmuch as other shapes such as square or rectangular could similarly be employed. At the distal end of the catheter advancer 30 is a radially-extending finger interface 301 configured to be pushed distally by the user (e.g., index finger) to advance the catheter 51 into the patient's vessel. The finger interface 301 may also be angled or curved for ergonomics and may additionally have a lip 308 to prevent the user's finger from slipping off. Textures, protrusions, indentations and the like may also be used on finger interface 301 without changing the invention. Finger interface 301 is preferably at least as wide and as tall as the tip of a small user's finger. Finger interface 301 is intended to be easy and comfortable to use by users with large, gloved fingers, so it is appropriately sized to accomplish this function. Should the user's finger have insufficient length to fully advance the catheter, the catheter advancer may have one or more additional finger tab(s) 302 along its length to provide grip or traction and/or incremental tactile indication of insertion depth to the user. At full advancement, the proximal flange 303 of the catheter advancer 30 abuts the proximal face of base 10 to stop advancement and is held in place in the fully forward configuration by detent clips 103 (see FIGS. 3, 6), which prevent proximal movement of catheter advancer 30. In the fully forward configuration, the catheter advancer 30 completely surrounds and encompasses the needle 20, including its sharp tip. Therefore, the clips 103 holding the catheter advancer 30 in the fully forward position allow the catheter advancer 30 to serve as a needle guard.

Figure 7:
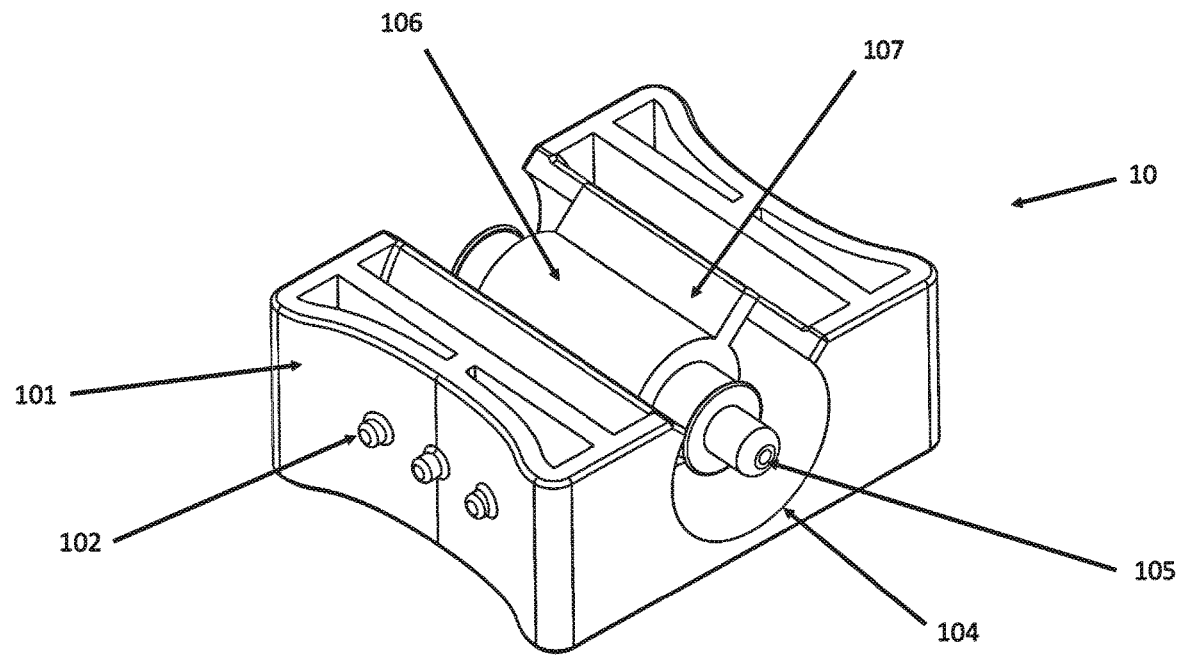
FIG. 7 is a top perspective illustration of a base of the intravenous access assist device.

In reference to FIG. 7, the needle 20 (not shown) is generally fixed in the base 10 relative to the three coordinate axes of the base 10 and held accordingly in needle interface 105 by mechanical means, which may include adhesive. The proximal end of the needle 20 resides in the flash chamber 106 of base 10, which is transparent. In this way, base 10 serves as the needle hub of a conventional intravenous access device. Flash chamber 106 is held in place within sliding channel 104 of base 10 by guiding tab 107. There may be more than one tab 107 for enhanced structural rigidity. Tab 107 also serves as a linear guide for the catheter advancer 30 as it slides through advancement channel 304. This linear guidance prevents rotation of catheter advancer 30 with respect to base 10. Similarly for the catheter assembly 50 that interfaces with the catheter advancer 30, there are mating features 307 on the distal end of catheter advancer 30 that fit within channels 504 of the proximal end 503 of the catheter hub 52. Note that the proximal end 503 of catheter hub 52 is generally fitted with luer lock threads.

In operation, from the "starting" configuration, the intravenous access assist device 1 (FIG. 2) has the tip of needle 20 exposed distal to the tip of catheter 51 in order to puncture a patient's tissue and vessel. After puncture is complete flash back will be visible in flash chamber 106. To facilitate visualization by the user, catheter advancer 30 has a window 305 that coincides with flash chamber 106, and movable component 40 has a window 402 that likewise coincides with flash chamber 106, such that flash back view is unobstructed. These components may also all be transparent to facilitate flash visualization and eliminate the need for windows 305 and 402 within the same invention.

Figure 5:
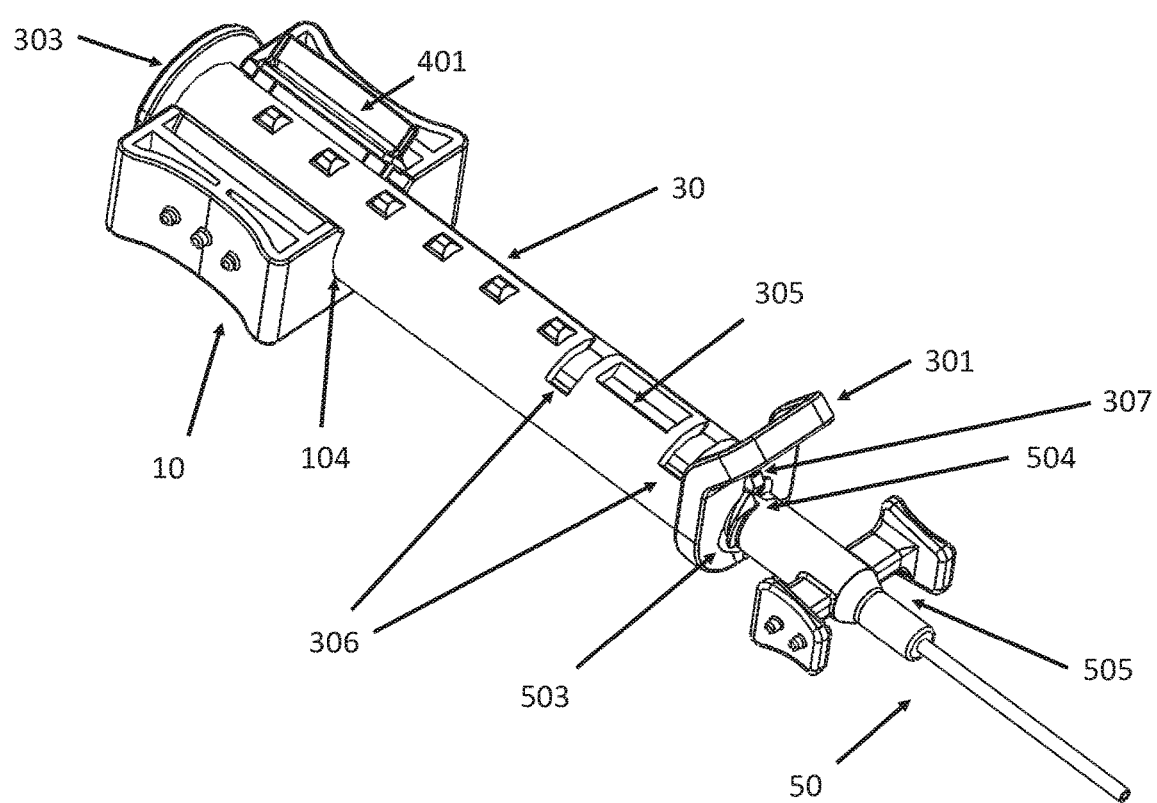
FIG. 5 is a top perspective illustration of the intravenous access assist device of the present invention in the "advanced" configuration.
Figure 6:
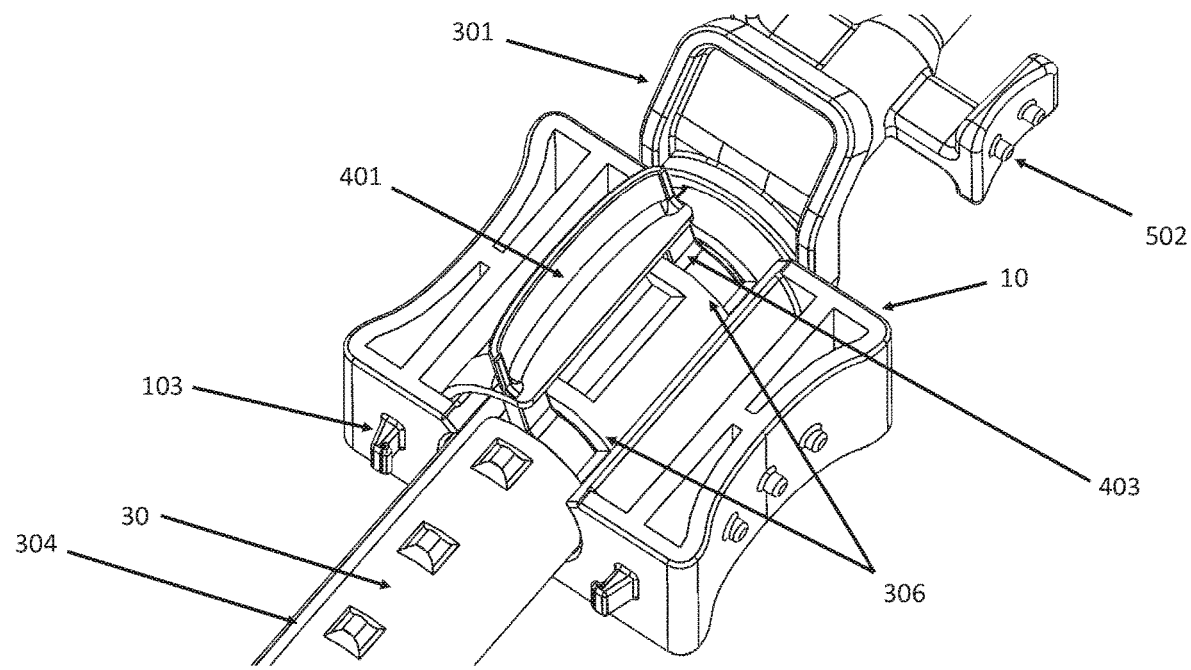
FIG. 6 is a close-up top perspective illustration of the intravenous access assist device of the present invention, showing the movable member in an intermediate position.

When the user is ready to advance the catheter 51, after viewing flash back through windows 402 and 305, the movable component 40 is moved from a first position (FIG. 2), wherein the catheter advancer 30 cannot be advanced, to a second position (FIG. 4), wherein the catheter advancer 30 can be advanced, by means of the finger interface 401. In this embodiment, pre-mature movement of the catheter advancer 30 is prevented as an operational safety feature to prevent the possible shearing of the catheter 51 prior to gaining intravenous access. Movement by means of slidable translation of catheter advancer 30 relative to base 10 is prevented by locking arms 403 of movable component 40, which reside in channels 306 of catheter advancer 30 (see FIG. 6). In this embodiment channels 306 are generally perpendicular to the needle length axis. Catheter advancer 30 is mechanically blocked by arms 403 until movable component 40 has been moved to the point where arms 403 coincide with guide tab 107 of base 10, which aligns with advancement channel 304 of catheter advancer 30. The catheter advancer can now be pushed distally by the user to fully advance the catheter assembly 50 and secure the needle 20, as shown in FIG. 5.

Figure 8:
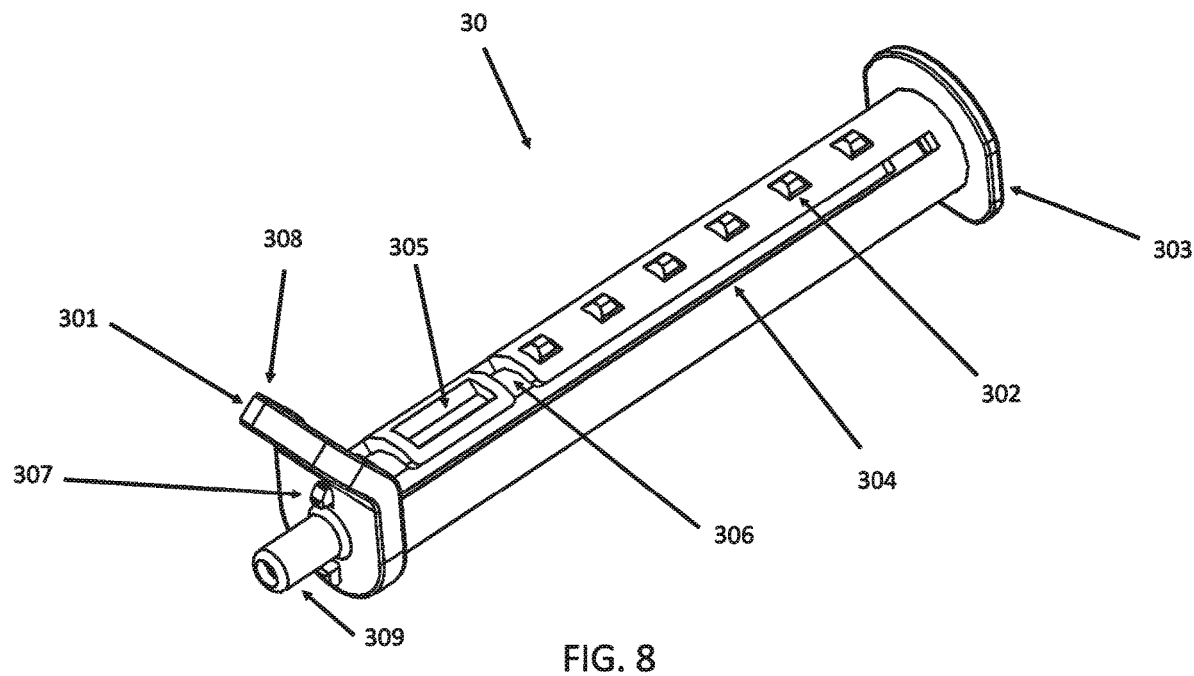
FIG. 8 is a top perspective illustration of a catheter advancer component of the intravenous access assist device.

Following advancement of the catheter assembly 50 and securement of the needle 20, the user removes the catheter assembly 50 from the catheter advancer 30 by gripping generally rigid, lateral finger interfaces 501. Finger interfaces 501 may be further fitted with protrusions 502 (FIG. 3) to enhance grip and tactile feedback, though other forms of texture may also be employed. Prior to removal in this embodiment, catheter hub 52 interfaces with catheter advancer 30 by frictional means with extension 309 and/or mating features 307, as shown in FIG. 8. When seated in the patient's vessel and the remainder of the device 1 has been removed from catheter assembly 50, securement of the catheter can be completed. Areas 505 created by generally rigid finger interfaces 501 facilitate such securement by providing sturdy backing.

FIGS. 1-8 showed a first embodiment of the invention wherein the safety feature engaged by movable component 40 was a mechanical constraint on movement of the catheter advancer 30 relative to the base 10. Similarly as would be obvious to those skilled in the art, movable component 40 could also be configured to engage, or directly interface with, a feature on the catheter assembly 50 such that the catheter assembly 50, in addition to the catheter advancer 30, cannot move relative to base 10 until allowed by movement of movable component from a first position to a second position as described above. Further, the movable component 40 may engage only the catheter assembly 50 instead of the catheter advancer 30, or the combination of both. These alternate operational safety features are considered within the scope and spirit of the invention.

As a secondary measure of coupling the translation of the catheter advancer 30 to the catheter assembly 50, alternate means could be employed such as a squeeze lock or a simple twisting or threading action. For example, threads 503 of catheter hub 52 could be used in this manner, as could channel(s) 504 of catheter hub 52, for engagement with similarly shaped mating features on catheter advancer 30. Under this scheme the movable component would engage either the catheter advancer 30 or catheter assembly 50, but not both. Then once the IV device 1 has properly placed the catheter assembly 50 into a patient's vessel through advancement of catheter advancer 30, the catheter assembly 50 could be disconnected from the catheter advancer 30 through the stated unlocking, twisting, or threading action. In the instance of twisting or threading, only a small amount would be necessary (e.g., less than 90 deg), though any amount could be used.

Figure 9:
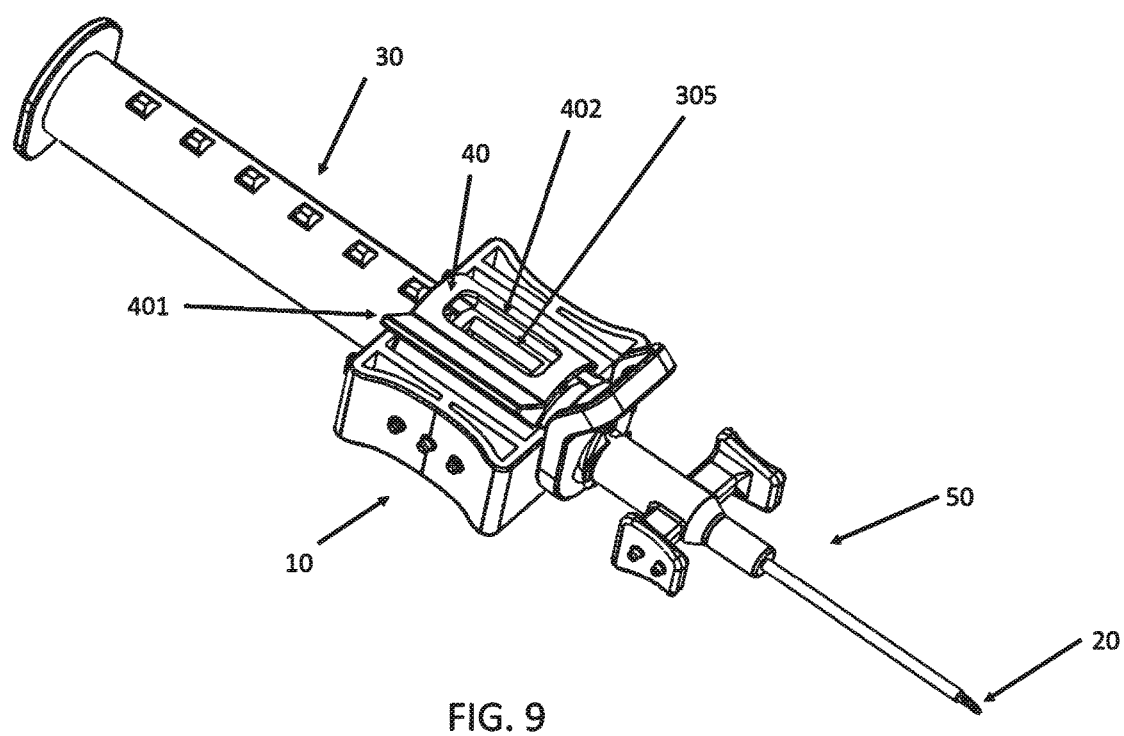
FIG. 9 is a top perspective illustration of a second embodiment of the intravenous access assist device of the present invention in the "starting" configuration.

Another embodiment of the intravenous access assist device 1 of the present invention may include another safety feature. In reference to FIGS. 9-10, movable component 40 still prevents relative motion between the catheter advancer 30 and base 10, but also rotates the needle 20 about its length axis as an additional safety feature to reduce the likelihood of making unintended punctures after the initial vessel puncture. When viewing FIG. 9 it can be seen that the tip of the needle 20 is down and ready to puncture, as this is the "starting" configuration. When viewing FIG. 10 it can be seen that the tip of the needle 20 has moved to a safer orientation in response to the movable component 40 being moved from a first position (e.g., "starting") to a second position (e.g., "ready to advance"). Of note, the catheter assembly 50 has not rotated with the needle 20 due to interference between mating feature 307 of catheter advancer 30 and channel(s) 504 of catheter hub 52. The catheter advancer 30 and catheter assembly 50 are identical to those described with FIGS. 1-8, and like components are like-numbered.

Figure 11:
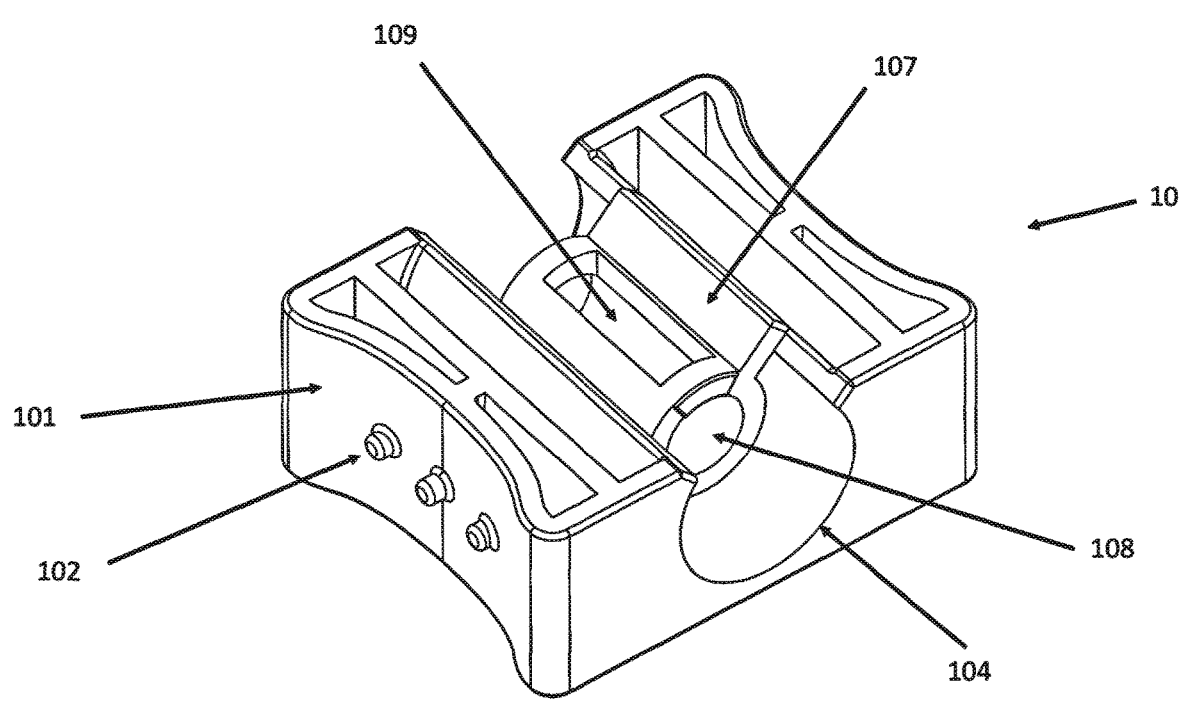
FIG. 11 is a top perspective illustration of a base of a second embodiment of the intravenous access assist device.

To enable this safety feature, the base 10 was modified as depicted in FIG. 11. While generally the same as FIG. 7, the needle interface 105 and flash chamber 106 were removed. In place of the former flash chamber 106 is now a flash chamber cavity 108 in which the flash chamber 404 is inserted. A flash viewing window 109 was also added to base 10 to coincide with windows 305 and 402 of the catheter advancer 30 and movable component 40, respectively, thereby providing clear view of flash back to the user. As stated previously, transparency of the base 10 may forgo the need for window 109.

Figure 12:
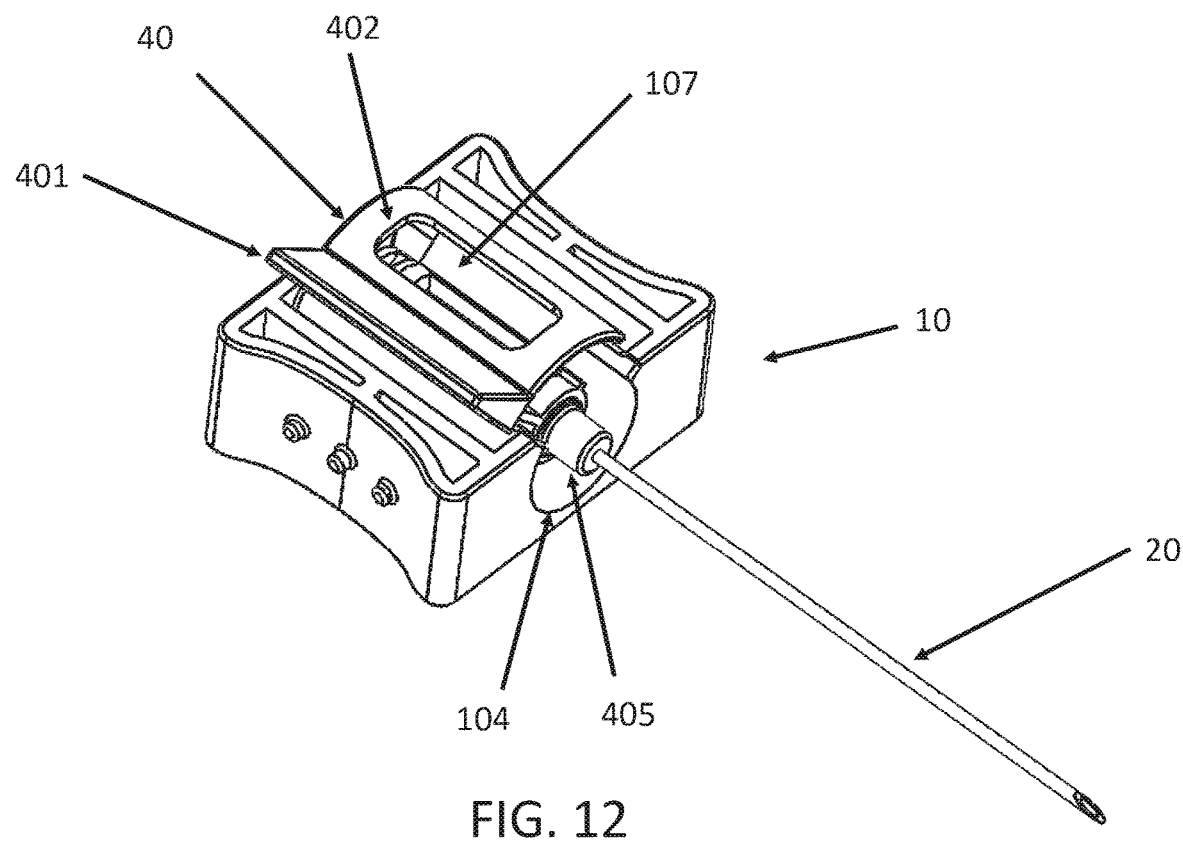
FIG. 12 is a top perspective illustration of a sub-assembly of a second embodiment of the intravenous access assist device in the "starting" configuration.
Figure 13:
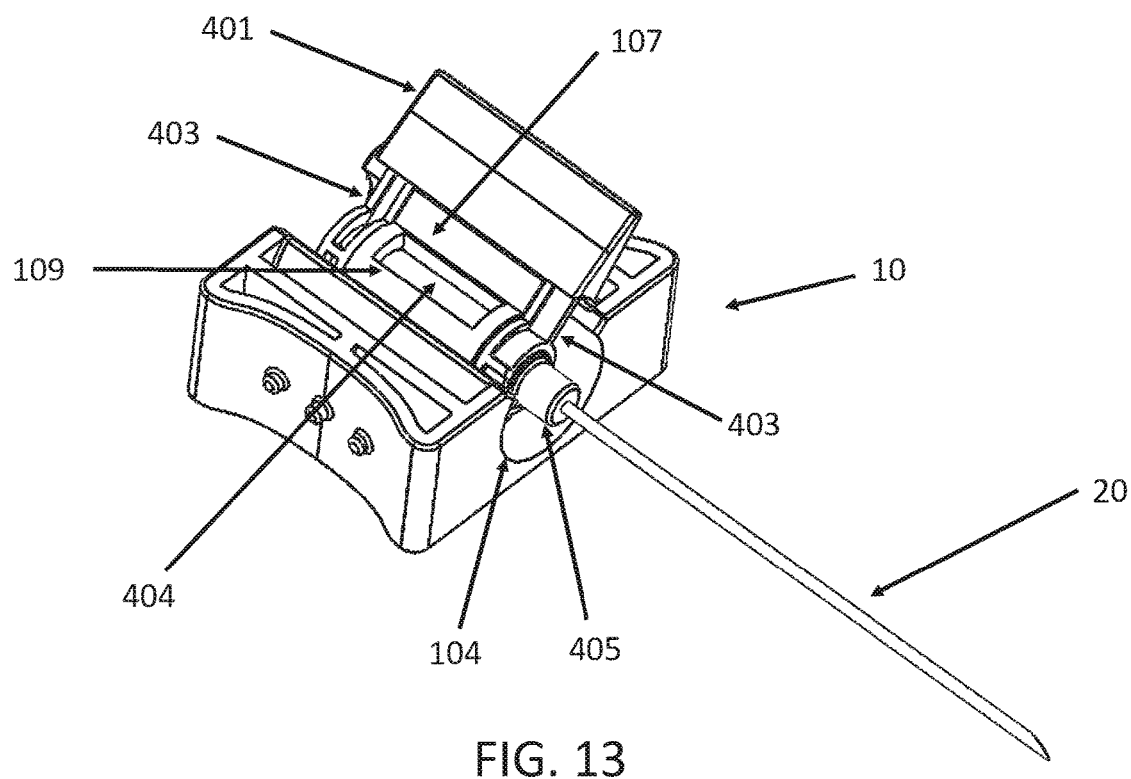
FIG. 13 is a top perspective illustration of a sub-assembly of a second embodiment of the intravenous access assist device in the "ready to advance" configuration.

As shown in FIGS. 12-13, the flash chamber 404 of this embodiment with a rotating needle is part of the movable component 40. Consequently, the needle 20 directly interfaces with needle interface 405 of movable component 40 and is mechanical fixed thereto. As described above, the needle, and flash chamber for this embodiment, does not translate in any direction relative to the base 10, but it can rotate about its length axis. Otherwise, the movable component 40 functions as above. The arms 403 prevent translation of the catheter advancer 30 relative to the base 10 until the user interacts with finger interface 401 of movable component 40, moving it until arms 403 align with guide tab 107 of base 10 such that channel 304 of catheter advancer 30 can be distally translated.

Figure 10:
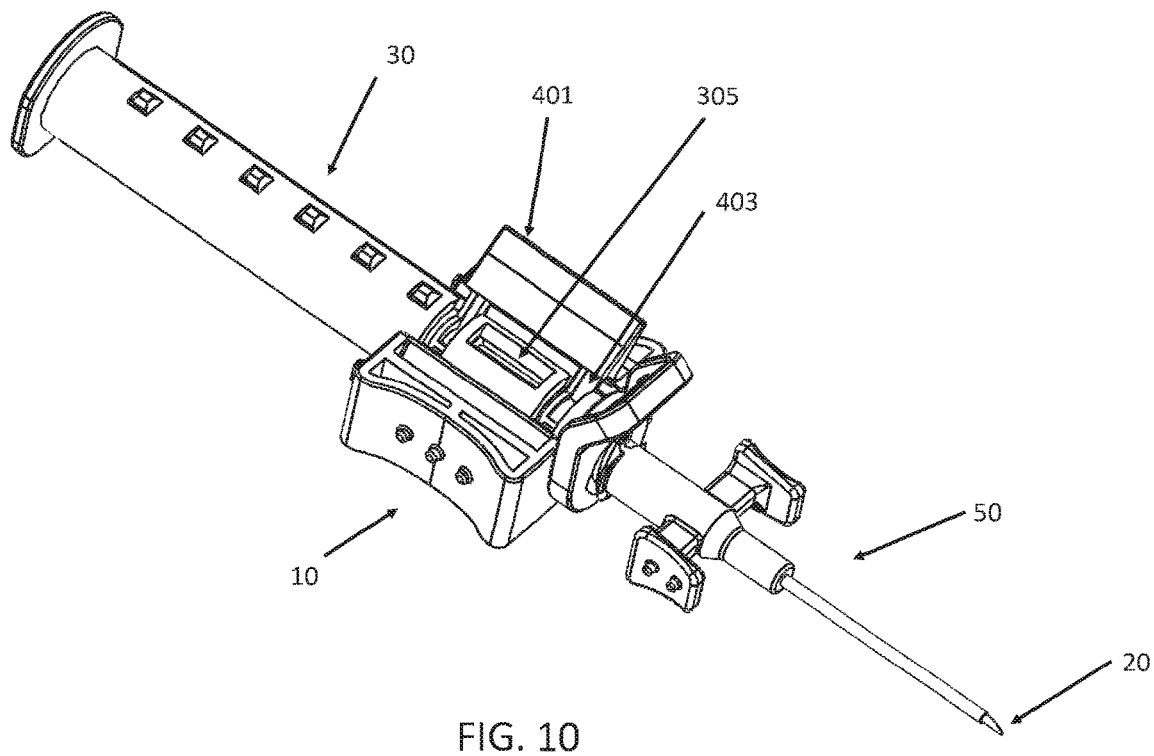
FIG. 10 is a top perspective illustration of a second embodiment of the intravenous access assist device of the present invention in the "ready to advance" configuration.

Yet another embodiment of the intravenous access assist device 1 of the present invention adds yet another safety feature that is engaged by movable component 40. In this embodiment, there is a catheter advancement lock and needle rotation as described above, as well as a minor advancement of the catheter, all engaged by movable component 40. The safety feature enabled with minor advancement of the catheter is a sheathing of the needle tip such that the incising end is covered by the catheter to prevent unintended trauma. When viewing FIG. 14 it can be seen that the catheter 51 and catheter advancer 30 are in the proximal-most position relative to base 10 with the tip of the needle 20 extending distally therefrom by a distance labeled A. This is the "starting" configuration, so the tip of needle 20 is down and ready to puncture. When viewing FIG. 15 it can be seen that the catheter advancer 30 and catheter assembly 50 have been advanced slightly, by a distance of approximately A, such that the distal end of catheter 51 covers the incising tip of needle 20. Note that in this embodiment the tip of the needle 20 has also rotated to a safer orientation in response to the movable component 40 being moved from a first position (e.g., "starting") to a second position (e.g., "ready to advance"), as shown in FIG. 10, though it is not visible in FIG. 15 because the catheter 51 has successfully sheathed the incising end of the needle 20. Note that sheathing advancement of needle 20 by catheter 51 can also be accomplished within the present invention without needle rotation. The catheter assembly 50 has also not rotated during these motions as described above. In this embodiment, the base 10, needle 20, and catheter assembly 50 are unchanged from what was described with FIGS. 9-13.

Figure 16:
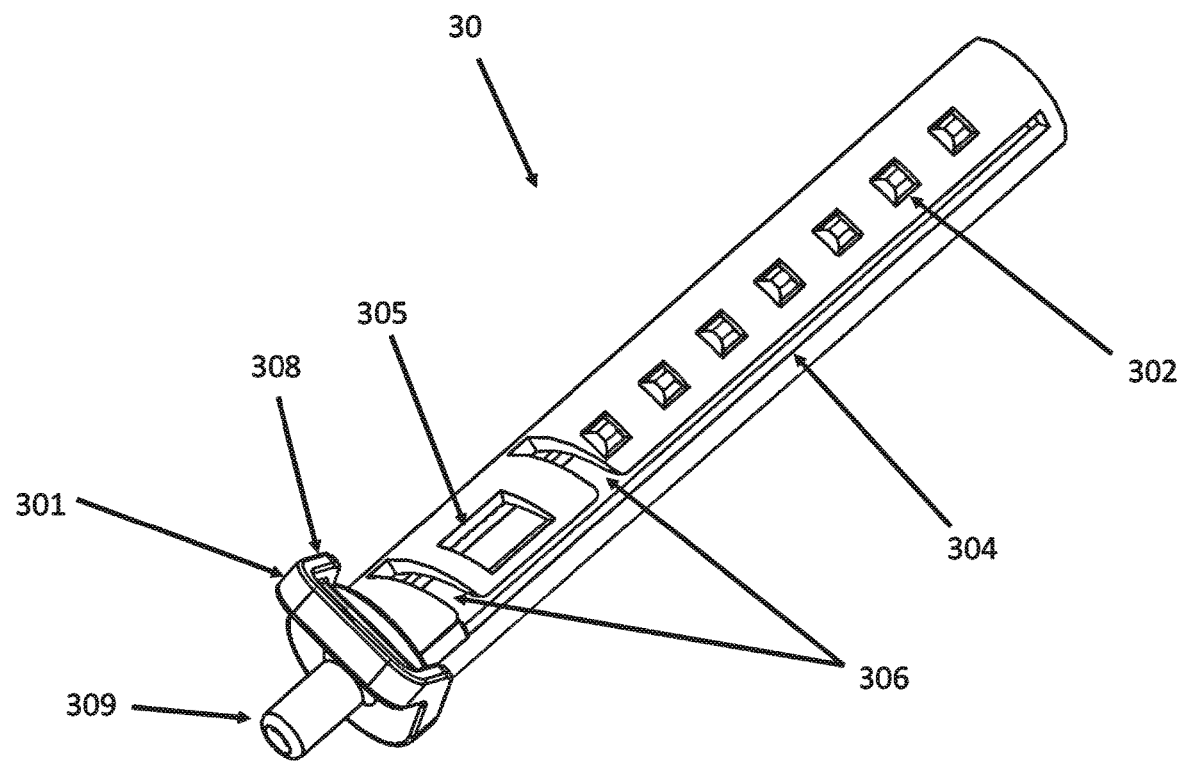
FIG. 16 is a top perspective illustration of a catheter advancer of a third embodiment of the intravenous access assist device.

In this embodiment, the catheter advancer 30 is the only component that was changed from the previously discussed embodiments, as shown in FIG. 16. The only change necessary to enable the minor sheathing advancement of catheter 51 over the tip of needle 20 is the orientation of channels 306. In the previously discussed embodiments these channels were generally perpendicular to the direction of catheter advancement, which is to say generally perpendicular to advancement guide channel 304. Translation of the catheter advancer 30, and therefore of catheter assembly 50, through engagement of movable component 40 is enabled by changing the angle such that the tip of the needle 20 is exposed for puncture in a first position, but is covered by the distal end of catheter 51 in a second position. The angle or slope of advancing channels 306 can be defined thusly. While it is not necessary that movable component 40 be changed from the previous embodiments to enable such sheathing advancement, it may be practical to change the orientation of arms 403 to more closely match that of the advancing channels 306 to facilitate their movement therein, or to employ cylindrical arms.

In contrast to changing the catheter advancer 30 to enable the sheathing advancement safety feature through movement of movable component 40, the base 10 and movable member 40 could be changed instead to create the same relative motion engaged by movable component 40. That is, channel(s) 306 of catheter advancer 30 could remain generally perpendicular to advancement guide channel 304 and movable component 40 could move along an angled path from a first position ("starting") to a second position ("ready to advance"), pushing the catheter advancer 30 and catheter assembly 50 distally in response. The attachment of arm(s) 403 to base 10 would simply need to be along a path or about an axis that is angled from the advancement axis, as would be obvious to those skilled in the art.

Figure 14:
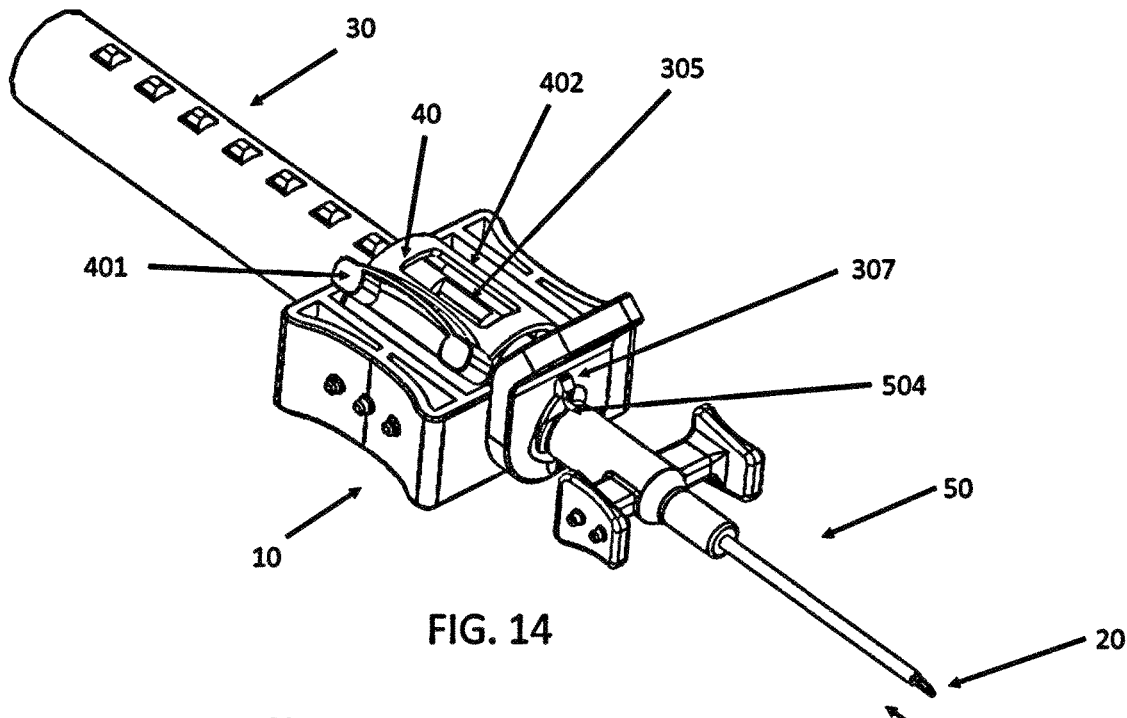
FIG. 14 is a top perspective illustration of a third embodiment of the intravenous access assist device of the present invention in the "starting" configuration.
Figure 15:
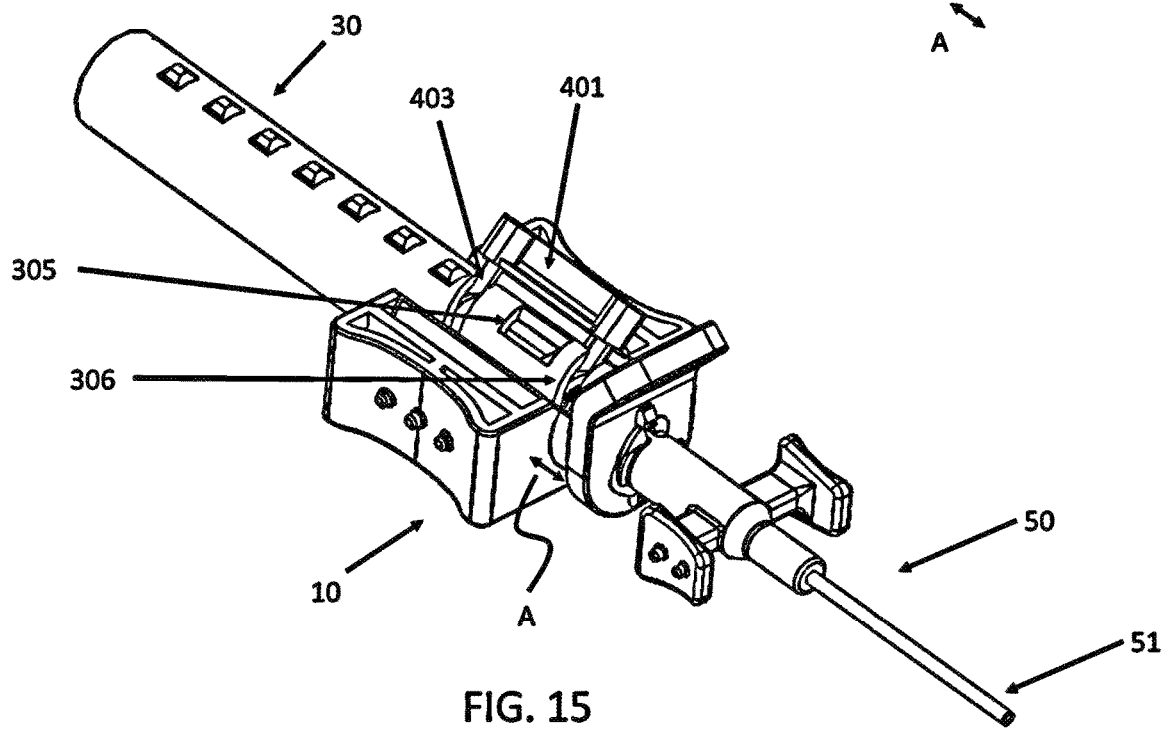
FIG. 15 is a top perspective illustration of a third embodiment of the intravenous access assist device of the present invention in the "ready to advance" configuration.

It should also be noted in reference to FIGS. 14-15 that catheter advancer 30 may not require flange 303, as is included in FIGS. 1-5 and 8-10. By way of excluding flange 303, clips 103 of base 10 would also not be required. Without flange 303, the catheter advancer 30 could be advanced such that the proximal end is either flush with the proximal end of base 10 or is somewhat distal to the proximal end of base 10, the physical translation limit being set by length of advancement channel 304. Holding of the catheter advancer 30 in the distal-most position such that it serves as a needle guard could then be enabled by standard one-way latches, for example. In this instance, the catheter advancer 30 or base 10 or both could have such latches within the same invention.

Note that while the movable component 40 described herein moved in a generally rotational manner relative to the base 10, it should be obvious to those skilled in the art that movable component 40 could also be configured to move in a non-rotational manner to accomplish the same functions without altering the invention to include linear or curvilinear motion paths. Similarly, various combinations or independent embodiments of the safety features described would be obvious to those skilled in the art and do not constitute a new invention. Examples may include but are not limited to catheter advancement without needle rotation, a lock engaging only the catheter hub instead of the catheter advancer, and minor advancement of the needle with or without the catheter and/or catheter advancer. Any manner of mechanisms implemented in connection with the movable member such that input motion by a user to movable component 40 is not equal to output motion of the safety feature is also obvious to those skilled in the art and includes such mechanisms as gears, racks, cams, and the like.

Figure 17:
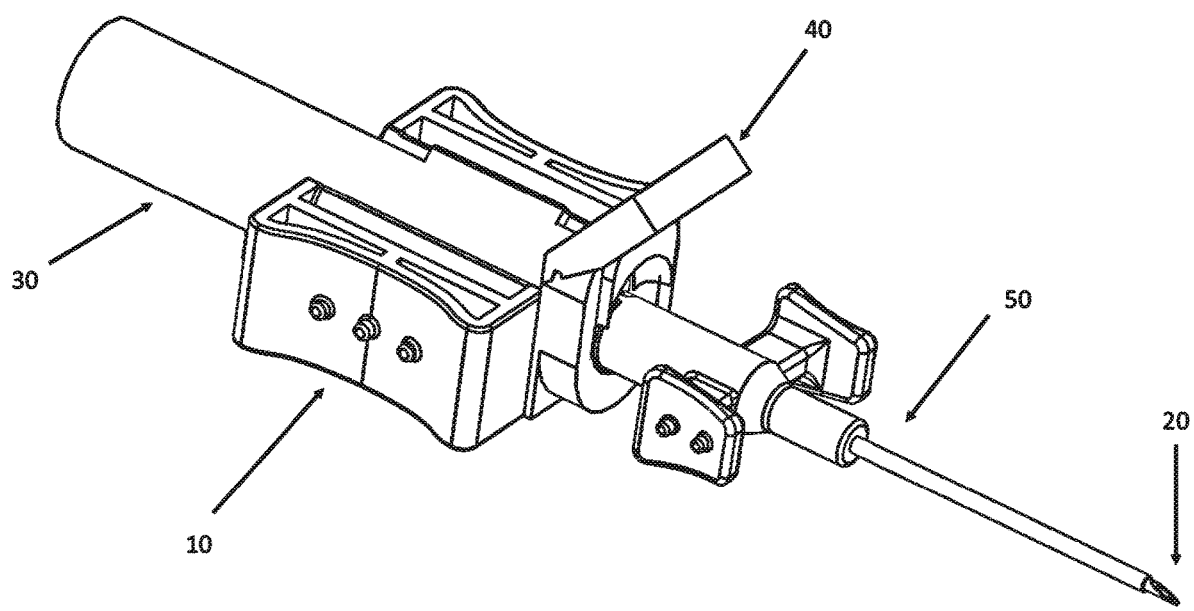
FIG. 17 is a top perspective illustration of a fourth embodiment of the intravenous access assist device of the present invention in the "starting" configuration.
Figure 18:
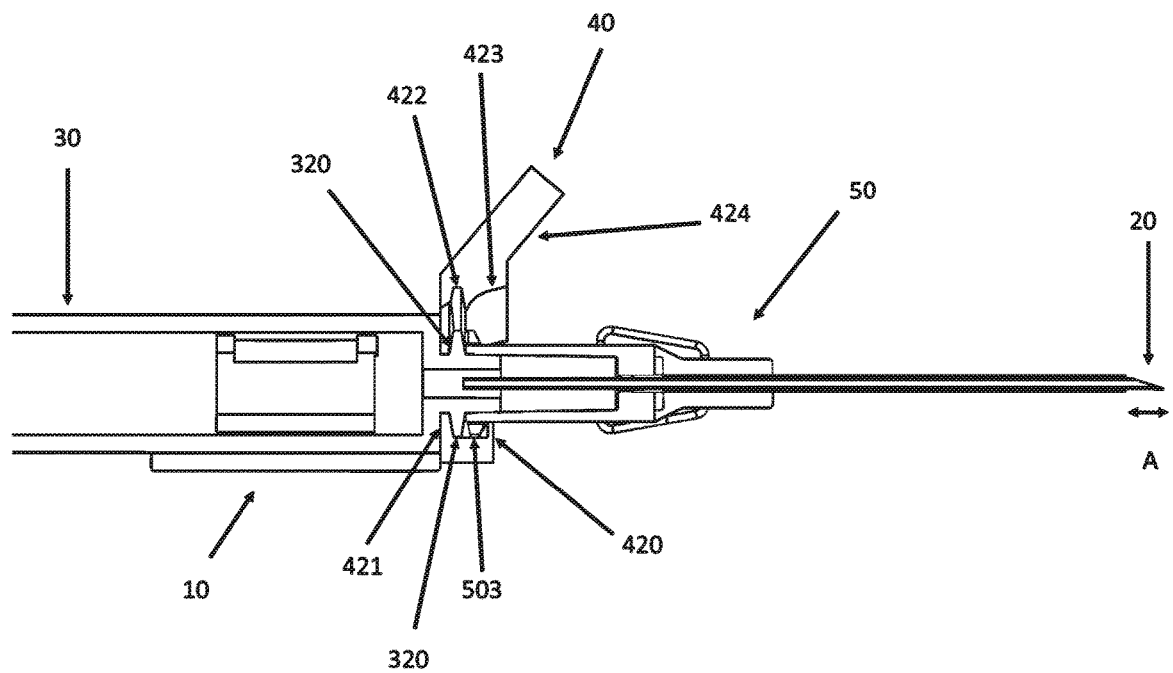
FIG. 18 is a side view, cross-sectional illustration of a fourth embodiment of the intravenous access assist device of the present invention in the "starting" configuration.
Figure 19:
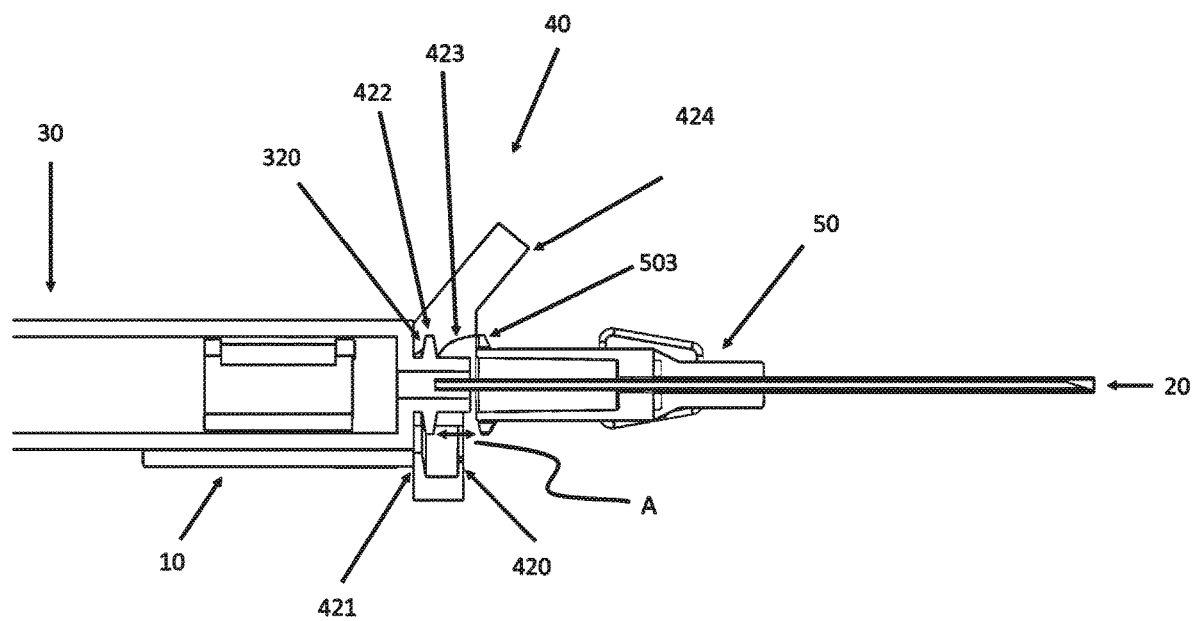
FIG. 19 is a side view, cross-sectional illustration of a fourth embodiment of the intravenous access assist device of the present invention in the "ready to advance" configuration.

Yet another embodiment employs a linear or curvilinear movement of movable component 40 from a first position to a second position to engage the same operational safety feature(s) as described above. As an example, consider the embodiment in FIG. 17, which has the same components of a base 10, needle 20, catheter advancer 30, movable component 40, and catheter assembly 50. Here the movable component 40 is in the "starting" configuration, as the movable component 40 is in its upward-most or first position. With reference to FIG. 18, the proximal-most end of catheter 503 is held in place relative to catheter advancer 30 in this configuration as distal lip 420 of movable component 40 prevents translation therefrom. In this way, movable component 40 locks the catheter assembly 50 to the catheter advancer 30 by holding proximal end 503 of catheter assembly 50 to extension 320 of catheter advancer 30 between distal lip 420 and proximal lip 421. While this embodiment does not additionally lock the catheter assembly 50 or catheter advancer 30 to base 10, this could easily be done and would be obvious to those skilled in the art.

When the user is ready to advance the catheter assembly 50, generally upward extending tab 424 of movable component 40 is pushed downward from the "starting" first position to a second position ("ready to advance"). In the second position (see FIG. 18), lips 420 and 421 have released or mechanically disengaged from holding catheter assembly 50 to catheter advancer 30. Cavity 422 of movable component 40 has now mechanically engaged extension 320 of catheter advancer 30 such that generally upward extending tab 424 serves the same advancement purpose as finger interface 301 in FIG. 2, for example. In this embodiment, such movement of movable component 40 from a first position to a second position also advances the catheter assembly 50 slightly distally by approximately a distance A such that the tip of needle 20 is effectively sheathed by the distal end of catheter 51. This sheathing or minor distal translation of catheter assembly 50 relative to catheter advancer 30 and/or needle 20 is enabled by advancing surface 423 of movable component 40. As movable component 40 is moved from a first position to a second position, surface 423 engages proximal end of catheter hub 503 and translates it distally.

It should now be apparent that the foregoing provides an easy-to-use IV placement assist device that is designed to facilitate and enhance safety of insertion of the needle and advancement of the catheter. The device enables greater control in the needle/catheter assembly for approach and advancement, facilitates small movements of the needle/catheter or either part individually, and prevents unwanted movement, all without interrupting the flow of the IV start procedure. This facilitates more efficient IV placement and success rates, and decreases vessel trauma, IV failure, and patient discomfort.

Having now fully set forth the preferred embodiments and certain modifications of the concept underlying the present invention, various other embodiments as well as certain variations and modifications thereto may obviously occur to those skilled in the art upon becoming familiar with the underlying concept. It is to be understood, therefore, that the invention may be practiced otherwise than as specifically set forth herein.

We claim:

1. An intravenous access device for inserting a catheter into a patient's vessel over a needle comprising:
   a base having opposing sides configured to be sidewardly gripped between two fingers and held thereby by a user, said base defining a cylindrical channel traversing said base along an axis, said cylindrical channel being at least partially open lengthwise along the axis;
   a needle assembly comprising a needle hub, and a needle fixed to said needle hub and having a distal incising end protruding from said needle hub along said axis;
   a catheter assembly that is slidably translatable over said needle, said catheter assembly comprising at least a proximal hub and a distal catheter, and
   a movable component rotationally-journaled into said base and constrained therein for limited rotation about said axis, said movable component being engaged to one of said needle hub or said catheter assembly such that rotation of said movable component from a first position to at least a second position controls relative motion of said needle hub or catheter assembly,
wherein rotation of said movable component translates said catheter assembly distally such that a distal end of said distal catheter sheaths said distal incising end of said needle.

2. An intravenous access device of claim 1 further comprising a catheter advancer component that interfaces with said proximal hub of said catheter assembly.

3. An intravenous access device of claim 2 wherein said catheter advancer component includes a distal finger advancement tab projecting distally and radially therefrom relative to an axis of said catheter advancement component.

4. An intravenous access device of claim 2, wherein said catheter advancer component is configured to encompass said needle as it slidably translates.

5. An intravenous access device of claim 4 wherein said catheter advancer component shrouds said needle incising end when said catheter advancer component is in a distal-most position relative to said base, thereby acting as a needle guard.

6. An intravenous access device of claim 4 wherein said base further comprises a detent mechanism for locking said catheter advancer component in a distal-most position relative to said base, wherein said distal end of said catheter advancer component covers said needle incising end to serve as a needle guard.

7. An intravenous access device of claim 4 wherein said movable component is configured to prevent relative motion between said catheter advancer component and said catheter assembly.

8. An intravenous access device of claim 2 wherein the catheter advancer component interfaces with said proximal hub of said catheter assembly to prevent rotation of said catheter assembly about said axis.

9. An intravenous access device of claim 2 wherein said catheter advancer further comprises a generally upward-extending advancement tab.

10. An intravenous access device of claim 1 wherein said movable component is configured to selectively lock said catheter assembly in a proximal-most position, and selectively unlock said catheter assembly to allow slidable translation of said catheter assembly along said axis.

11. An intravenous access device of claim 10 wherein slidable translation between said base and said catheter assembly is constrained in at least one degree of freedom.

12. An intravenous access device of claim 1 wherein said movable component is configured to selectively lock said catheter assembly relative to said base when said catheter assembly is in a proximal-most position, and selectively unlock said catheter assembly to allow slidable translation of said catheter assembly along said axis.

13. An intravenous access device of claim 12 wherein said slidable translation between said base and said catheter assembly is constrained in at least one degree of freedom.

14. An intravenous access device of claim 1 wherein rotation of said movable component rotates said needle about said axis relative to said base.

15. An intravenous access device of claim 1 wherein rotation of said movable component rotates said needle about said axis relative to said catheter assembly.

16. An intravenous access device of claim 1 further comprising a flash chamber window configured for viewing blood flashing back upon insertion of said distal incising end into a vessel.

17. An intravenous access device of claim 1 wherein said base has at least one contoured finger grip.

18. An intravenous access device of claim 17 wherein said finger grip is textured.

19. An intravenous access device of claim 1 wherein said proximal hub of said catheter assembly further comprises at least one laterally extending and generally rigid finger grip.

20. An intravenous access device of claim 19 wherein said finger grip is contoured and textured.

21. An intravenous access device of claim 19 wherein said proximal hub of said catheter assembly and laterally extending finger grip form a channel configured for insertion and securement of the inserted catheter assembly.

22. An intravenous access device of claim 1 wherein said movable component is configured to selectively lock said catheter assembly at any position along said needle, and selectively unlock said catheter assembly to allow relative sliding motion of said catheter assembly along said axis.

23. An intravenous access device of claim 1 wherein rotation of said movable component prevents said needle from extending distally relative to said catheter.

24. An intravenous access device for inserting a catheter into a patient's vessel over a needle comprising:
a base having opposing sides configured to be sidewardly-gripped between two fingers and held thereby by a user, said base defining an internal channel extending along an axis, said internal channel being at least partially open lengthwise along the axis;
a needle fixed to a needle hub and having a distal incising end protruding from said needle hub along said axis;
a catheter assembly comprising at least,
a catheter hub, and
a distal catheter protruding from said catheter hub;
a catheter advancer that interfaces with said catheter hub of said catheter assembly;
a movable component rotationally-journaled into said base protruding from the at least partially open internal channel of said base and constrained therein for limitation about said axis, said movable component being engaged to one of said needle hub or said catheter assembly and configured such that selective rotation of said movable component from a first position to a second position translates said catheter assembly distally such that a distal end of said distal catheter sheaths said distal incising end of said needle.

25. An intravenous access device of claim 24 wherein said movable component affects movement of one or more additional components that initiate an operational safety feature.

26. An intravenous access device of claim 25 wherein said operational safety feature comprises preventing relative sliding motion of said catheter assembly along said needle.

27. An intravenous access device of claim 25 wherein said one or more additional components are comprised of threads, gears, radial slots, circumferentially angled slots, or axial slots.

28. An intravenous access device of claim 25 wherein said operational safety feature comprises translating said catheter assembly distally until a distal end of said catheter covers said distal incising end of said needle.

29. An intravenous access device of claim 25, wherein said operational safety feature comprises rotation of said needle about said axis relative to said base.

30. An intravenous access device of claim 25, wherein said operational safety feature comprises rotation of said needle about said axis relative to said catheter assembly.

31. An intravenous access device of claim 25, wherein said operational safety feature comprises preventing said needle from extending distally relative to said catheter.

* * * * *